(12) United States Patent
Lim et al.

(10) Patent No.: US 8,858,897 B2
(45) Date of Patent: Oct. 14, 2014

(54) MICROFLUIDIC CHIP FOR ANALYSIS FOR FLUID SAMPLE

(75) Inventors: Hyun Chang Lim, Seoul (KR); Jun Ha Park, Suwon-si (KR); Chang Seop Lee, Ansan-si (KR); Hyun Joo Jung, Seoul (KR); Ji Young Park, Seoul (KR); Chan Il Chung, Seoul (KR); Jun Keun Chang, Seoul (KR)

(73) Assignee: Nanoentek, Inc., Seoul (KR)

( * ) Notice: Subject to any disclaimer, the term of this patent is extended or adjusted under 35 U.S.C. 154(b) by 1083 days.

(21) Appl. No.: 12/667,372

(22) PCT Filed: Nov. 21, 2008

(86) PCT No.: PCT/KR2008/006862
§ 371 (c)(1),
(2), (4) Date: Jul. 13, 2011

(87) PCT Pub. No.: WO2009/066948
PCT Pub. Date: May 28, 2009

(65) Prior Publication Data
US 2012/0003725 A1      Jan. 5, 2012

(30) Foreign Application Priority Data
Nov. 22, 2007   (KR) .................. 10-2007-0119506

(51) Int. Cl.
*B01L 99/00* (2010.01)
*B01L 3/00* (2006.01)
*G01N 35/00* (2006.01)
*G01N 33/53* (2006.01)

(52) U.S. Cl.
CPC .... *G01N 35/00029* (2013.01); *B01L 3/502746* (2013.01); *B01L 2400/0406* (2013.01); *G01N 2035/00158* (2013.01); *B01L 2400/086* (2013.01); *B01L 2300/0825* (2013.01); *G01N 33/5304* (2013.01); *B01L 2300/087* (2013.01); *B01L 2300/089* (2013.01); *B01L 3/502723* (2013.01)
USPC ............................................ 422/507

(58) Field of Classification Search
CPC ............. G01N 2035/00158; B01L 3/502746; B01L 2300/087; B01L 2300/089; B01L 2400/0406
USPC ................... 422/502, 503, 504, 507
See application file for complete search history.

(56) References Cited

U.S. PATENT DOCUMENTS
6,663,833 B1 * 12/2003 Stave et al. ............... 422/81
2007/0269893 A1   11/2007 Blankenstein et al.

FOREIGN PATENT DOCUMENTS
EP       1 385 002        1/2004
JP       03-223674        10/1991
(Continued)

OTHER PUBLICATIONS
Office Action for Japanese Application No. 2010-514653.
Extended European Search Report for European Application No. 08852470.7 (Apr. 13, 2012).
Kim KS, et al.; PubMed; "magnetic force-based multiplexed immunoassay using superparamagnetic nanoparticles in microfluidic channel"; PMID: 15915258; 2005.
(Continued)

*Primary Examiner* — Paul Hyun
(74) *Attorney, Agent, or Firm* — Sherr & Jiang, PLLC

(57) ABSTRACT

Disclosed is a microfluidic chip capable of accurately and quickly detecting presence of a trace amount of a target within a fluid sample. It has a channel structure comprising a sample inlet for feeding a sample therethrough, a first reservoir for primarily storing the sample therein, a second reservoir for secondarily storing the sample therein, a first reaction portion in which a target is conjugated with a label, a second reaction portion in which the labeled target undergoes a specific reaction, such as an antigen-antibody reaction, and a delaying portion, located between the first and the second reaction portion, for decreasing a flow rate of the sample.

8 Claims, 2 Drawing Sheets

(56) References Cited

FOREIGN PATENT DOCUMENTS

| JP | 2005-156556 | 6/2005 |
| KR | 1020060017701 | 2/2006 |
| KR | 1020060053183 | 5/2006 |
| WO | 2005/119211 | 12/2005 |
| WO | 2006/022495 | 3/2006 |

OTHER PUBLICATIONS

International Search Report from Application No. PCT/KR2008/006862 mailed on Jun. 5, 2009.

Satao K., et al.; "Microchip-based enzyme-linked immunosorbent assay (microELISA) system with thermal lens detection" Lab Chip, www.rsc.org/loc; 2004.

* cited by examiner

Distance between front and rear ends of interface

MICROFLUIDIC CHIP FOR ANALYSIS FOR FLUID SAMPLE

CROSS-REFERENCES TO RELATED APPLICATIONS

This application is a U.S. national phase application, pursuant to 35 U.S.C. §371 of PCT/KR2008/006862, filed Nov. 21, 2008, designating the United States, which claims priority to Korean Application No. 10-2007-0119506, filed Nov. 22, 2007. The entire contents of the aforementioned patent applications are incorporated herein by this reference.

TECHNICAL FIELD

The present invention relates to a microfluidic chip capable of accurately and quickly detecting presence of a trace amount of a target within a fluid sample. More particularly, the present invention relates to a microfluidic chip for the analysis of a fluid sample, having a channel structure comprising a sample inlet for feeding a sample therethrough, a first reservoir for primarily storing the sample therein, a second reservoir for secondarily storing the sample therein, a first reaction portion in which a target is conjugated with a label, a second reaction portion in which the labeled target undergoes a specific reaction, such as an antigen-antibody reaction, and a delaying portion, located between the first and the second reaction portion, for decreasing a flow rate of the sample.

BACKGROUND ART

The analysis of fluid samples is widely used in the chemical and bioengineering fields as well as in the medical field to clinically diagnose diseases using blood and humoral liquids from patients. For more convenient and efficient analysis of fluid samples, various small diagnostic devices have been developed and utilized. Particularly, a lab-on-a-chip is a device that integrates various laboratory functions such as separation, filtration, mixing, labeling, analyzing, washing, etc., on a small single chip.

While passing through microchannels formed on a chip, fluid samples are allowed to undergo the laboratory mechanisms and are finally detected by means of, for example, a fluorescent label indicating a reaction with an antibody immobilized onto the chip. Thus, it is one of the most important technical factors in quickly obtaining accurate analysis results by use of such miniaturized chips to control the motion of fluid samples through the microchannels formed on the chips.

A driving force to move fluid through the microchannels on a chip may be generated by a small motor or may resort to capillary phenomena. In the case of a chip using capillary phenomenon as a main driving force, the fluid flowing through the microchannels shows irregular and non-uniform mobility patterns, particularly when the microchannels are of extremely low height or are narrowed. These irregular and non-uniform mobility patterns are generated due to the differences in fluid interaction with upper and lower walls and with left and right walls and act as a great hindrance to detecting and analyzing a target contained in a trace amount in the fluid sample.

Also, when closed channels of tens of micrometers in size are formed, it is not easy to uniformly process edge portions of channels without loss, thus causing problems in dimension and quality upon mass-scale production. This minute difference in channel structure disturbs fluid flow, leading to an inconsistent analysis result.

To overcome such problems, Korean Patent Application No. 10-2007-0073659, filed on Jul. 23, 2007, suggests a chip in which one of a pair of inner sidewalls of a channel is adjacent to an extension portion which is more deeply depressed than the channel, so that fluid passes through the channel, with interaction with only the other inner sidewall.

Korean Patent Application No. 10-2007-0073657, filed on Jul. 23, 2007, suggests the effective removal of noise only through microchannel structures and without the use of paper filters or porous membranes, thus quickly performing both quantitative and qualitative analyses with a trace amount of fluid sample.

However, when wall-free, microfluidic chips associated with the above-mentioned techniques are employed, it is necessary to appropriately control the flow of fluid at each step.

For example, as suggested in Korean Patent Application No. 10-2007-0073657, when a fluid sample is fed through a sample inlet into a reservoir, it moves into the microchannels because of fluid pressure and capillary phenomenon, with the concomitant noise filtering of the sample, e.g., blood. In contrast, when fluid is directly introduced into a microchannel of a size on the micro scale, the fluid filling the reservoir has a pressure sufficiently large to spread over the extension portion. Thus, it impedes the wall-free effect suggested by Korean Patent Application No. 10-2007-0073659, resulting in the bringing of errors into the analysis results.

A reaction portion is generally designed to be a site where a label, such as a fluorescent material, is bound to a target and the labeled target undergoes a specific reaction such as an antigen-antibody reaction, so as to activate the label. For accurate qualitative and quantitative analyses, the sample must reside in the reaction portion long enough to sufficiently react with, for example, an antibody.

Therefore, unless the flow of the fluid across the reaction portion is controllably delayed during passage therethrough, an error may occur in the qualitative and quantitative analyses of a target within the fluid. That is, it is necessary to slow the flow rate of the fluid across the reaction portion. At this time, the reaction efficiency may be further increased if reaction samples are mixed.

Leading to the present invention, intensive and thorough research into a microfluidic wall-free chip, conducted by the present inventor, resulted in successfully preventing a sample from leaking into the extension portion upon the introduction thereof into the microchannel and in delaying the flow rate of the fluid enough so that it could sufficiently react therein with the concomitant mixing of reaction samples.

DISCLOSURE OF INVENTION

Technical Problem

It is an object of the present invention to provide a microfluidic wall-free chip in which when a fluid sample is driven to proceed into a microchannel by the pressure thereof and capillary phenomenon after being fed through a sample inlet into a reservoir, the fluid is prevented from leaking to an extension portion due to the fluid pressure within the reservoir, thus guaranteeing the wall-free effect.

It is another object of the present invention to provide a microfluidic wall-free chip in which a sample is prevented from quickly passing through a reaction portion, thus allowing a target to reside in the reaction portion sufficiently long enough to react with a detecting material.

It is a further object of the present invention to provide a microfluidic wall-free chip in which reaction samples are suitably conducted during the passage of an analysis sample through a microchannel so as to achieve analysis more efficiently.

Technical Solution

In accordance with an aspect thereof, the present invention provides a microfluidic chip for analyzing a fluid sample, having a channel structure comprising: a sample inlet for feeding the sample therethrough; a first reservoir for primarily storing the sample therein; a first reaction portion in which a target is conjugated with a label; a second reaction portion in which the labeled target undergoes a specific reaction, such as an antigen-antibody reaction; and a delaying portion, located between the first and second reaction portions, for decreasing a flow rate of the sample.

In accordance with another aspect thereof, the present invention provides a microfluidic chip for analyzing a fluid sample, having a channel structure comprising: a sample inlet for feeding the sample therethrough; a first reservoir for primarily storing the sample therein; a second reservoir for secondarily storing the sample therein; a first reaction portion in which a target is conjugated with a label; and a second reaction portion in which the labeled target undergoes a specific reaction, such as an antigen-antibody reaction.

In accordance with a further aspect thereof, the present invention provides a microfluidic chip for analyzing a fluid sample, having a channel structure comprising: a sample inlet for feeding the sample therethrough; a first reservoir for primarily storing the sample therein; a second reservoir for secondarily storing the sample therein; a first reaction portion in which a target is conjugated with a label; a second reaction portion in which the labeled target undergoes a specific reaction, such as an antigen-antibody reaction; and a delaying portion, located between the first and second reaction portions, for decreasing a flow rate of the sample.

Advantageous Effects

As described above, the microfluidic chip in accordance with the present invention is designed to prevent the fluid sample from leaking to the extension portion upon the introduction of the sample into the microchannel so as to afford a sufficient wall-free effect to the extension portion. Also, the microfluidic chip according to the present invention allows the sample to reside in the reaction portion long enough to react with reagents and to exert a sufficient mixing effect.

Therefore, the microfluidic chip of the present invention guarantees accurate and quick qualitative and quantitative analyses of a trace amount of a sample without volumetric loss.

BEST MODE FOR CARRYING OUT THE INVENTION

Figure 1:
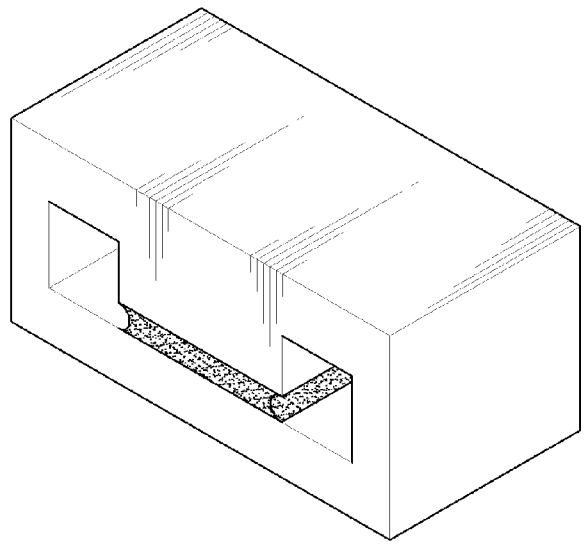
FIG. 1 is a conceptual view showing the operational principle of a wall-free microchannel in accordance with the present invention.

Reference should now be made to the drawings, in which the same reference numerals are used throughout the different drawings to designate the same or similar components.

The term closed channel, as used herein, is intended to refer to a tube structure formed by upper, lower, right and left inner walls within the chip, which is designed to allow a fluid to flow therethrough without leaking to the outside.

The term wall-free channel, as used herein, is intended to refer to a channel in which one of a pair of inner sidewalls is adjacent to an extension portion which is more deeply depressed than the channel, so that fluid passes through the channel, with interaction with only the other inner sidewall because fluid flowing through the microchannels shows irregular and non-uniform mobility patterns due to the differences between fluid interaction with upper and lower walls and with left and right walls (FIG. 1). With regard to more details, reference may be made to Korean Patent Application No. 10-2007-0073659.

Embodiment 1

Figure 2:
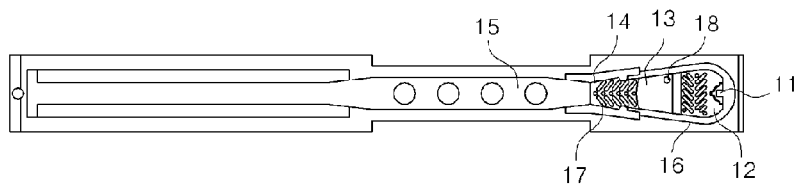
FIG. 2 is a schematic plan view showing a microfluidic chip according to a first embodiment of the present invention.

A microfluidic chip for analyzing fluidic samples in accordance with a first embodiment of the present invention, as shown in FIG. 2, has a channel structure comprising a sample inlet 11 for feeding a sample therethrough, a first reservoir 12 for primarily storing the sample therein, a second reservoir 13 for secondarily storing the sample therein, a first reaction portion 14 in which a target is conjugated with a label, and a second reaction portion 15 in which the labeled target undergoes a specific reaction, for example, an antigen-antibody reaction.

In this channel structure, the first reservoir is a chamber for accommodating the fluidic sample fed through the inlet and the second reservoir is also a chamber for storing the sample secondarily. From the second reservoir, the sample is moved through a wall-free microchannel leading to a reaction portion. A suitably controlled height of the microchannel allows noise of the sample to be filtered off without the use of paper filter or a porous membrane during the passage of the sample therethrough, thus minimizing the volumetric loss rate of the sample.

The height of the microchannel depends on the kinds of sample used. For instance, when whole blood in quantities smaller than 100 µL is used, the height of the channel may be set to range from about 1 to 20 µm to filter off noise such as red blood cells and white blood cells. With regard to more details, reference may be made to U.S. Ser. No. 12/667,374 (published as U.S. Patent Application Publication US 2011/0294197), which corresponds to Korean Patent Application No. 10-2007-0073657.

However, when a sample is introduced into the extension portion-provided wall-free microchannel of ones to tens of micrometers in width just after filling the first reservoir, as disclosed in the patent application supra, it is likely to leak to the extension portion adjacent to the microchannel due to the pressure ($P=gh$) and surface tension of the sample filling the reservoir. This disrupts the wall-free function, ultimately bringing about an error in the analysis result.

Figure 3:
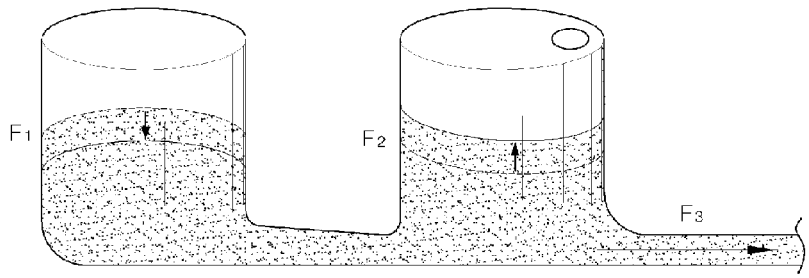
FIG. 3 is a conceptual view showing the operational principle of the first and the second reservoir.

In order to circumvent this problem, an additional reservoir is provided between a first reservoir connected with a sample inlet and a wall-free microchannel leading to a reaction portion in accordance with a first embodiment of the present invention. At an upper side of this secondary reservoir is located a hole 18 for ventilating air from the reservoir to the outside. While the sample fills the secondary reservoir after completely filling the first one, the force of the fluid pressure between the two reservoirs ($F_1$ and $F_2$) balances out, during which the pressure ($F_3$) of the sample flowing into the wall-free microchannel is suitably controlled so as to prevent the sample from leaking to the extension portion (FIG. 3).

Also, the passage of the sample through the second reservoir enjoys the advantage of homogenously mixing the sample with a meniscus. As seen in FIG. 2, various patterns 16 are formed on the bottom of the reservoir to improve the mixing effect.

Until the sample comes out of the second reservoir, it flows through the closed channel. Sealing work is not needed to form the closed channel. An effective, fluid-tight, closed channel can be obtained simply by assembling the upper and lower substrates.

After passage through the second reservoir, the sample is driven and flows toward the first reaction portion in which it reacts with a label, such as a fluorescent material, and then toward the second reaction portion in which it undergoes a specific reaction such as an antigen-antibody reaction. A target of interest labeled with, for example, a fluorescent material in the first reaction portion is reacted with, for example, an antibody in the second reaction portion, with the activation of the label bound to the target. This activated label, such as a fluorescent material, is detected by a separate device, such as an optical detector, for qualitative and quantitative analysis. As seen in FIG. 2, various patterns 17 may be formed on the bottom of the reaction portion to increase the surface area of the reaction materials and to improve the mixing effect.

Embodiment 2

Figure 4:
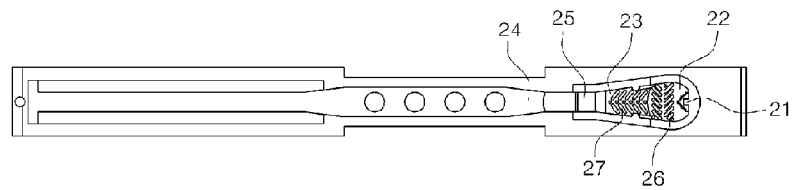
FIG. 4 is a schematic plan view showing a microfluidic chip according to a second embodiment of the present invention.

With reference to FIG. 4, a microfluidic chip for analyzing liquid samples in accordance with a second embodiment of the present invention will be described as shown. As seen in FIG. 2, the microfluidic chip has a channel structure comprising a sample inlet 21 for feeding a sample therethrough, a first reservoir 22 for primarily storing the sample therein, a first reaction portion 23 in which a target is conjugated with a label, a second reaction portion 24 in which the labeled target undergoes a specific reaction, for example, an antigen-antibody reaction, and a delaying portion 25, located between the first and the second reaction portions, for decreasing the flow rate of the sample.

In this embodiment, after being fed through the inlet and filling the reservoir, the sample flows into the first reaction portion through the wall-free microchannel. Then, when the sample immediately advances from the first reaction portion for the labeling reaction to the second reaction portion for a specific reaction such as an antigen-antibody reaction, the sample may move too quickly to guarantee the specific reaction, resulting in an error in the qualitative and quantitative analyses of the target. Accordingly, it is necessary to retard the progression of the sample into the second reaction portion.

Figure 5:
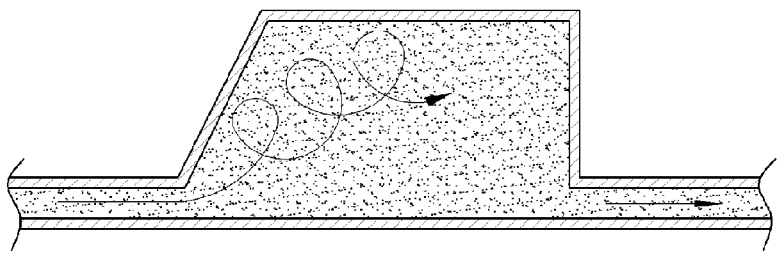
FIG. 5 is a conceptual view showing the operational principle of a delaying portion.

To this end, a delay portion for decreasing the flow rate of fluid is provided between the first and second reaction portions in accordance with this embodiment of the present invention. The delaying portion, as shown in FIG. 5, has a slant side which becomes ascendant as it goes from the first reaction portion to the delay portion and a slant or vertical side which become descendant as it goes toward the second reaction portion. The sample runs along the slant side from the microchannel of the first reaction portion to the delay portion. After reaching the slant or vertical side of the delaying portion, the sample proceeds to the microchannel of the second reaction portion. Having a chamber configuration and a large volume, the delaying portion exhibits both delaying and mixing effects.

The slant side of the delaying portion may vary in inclination and shape, depending on the hydrophilicity of the surface of the flow path as well as the properties of the sample. Preferably, the slant side of the delaying portion has an inclination of less than the contact angle indicating the hydrophilicity of the surface of the flow path, which ranges from 5 to 60 C.

For example, if the inclination exceeds the upper limit of the angle range, sufficient driving force is not applied to the fluid so that the flow ceases. On the other hand, if the inclination is too small, the fluid does not stay sufficiently long enough in the delaying portion, but proceeds to the second reaction portion, thus producing only an insufficient delaying effect or requiring a large length of the flow path.

Figure 7:
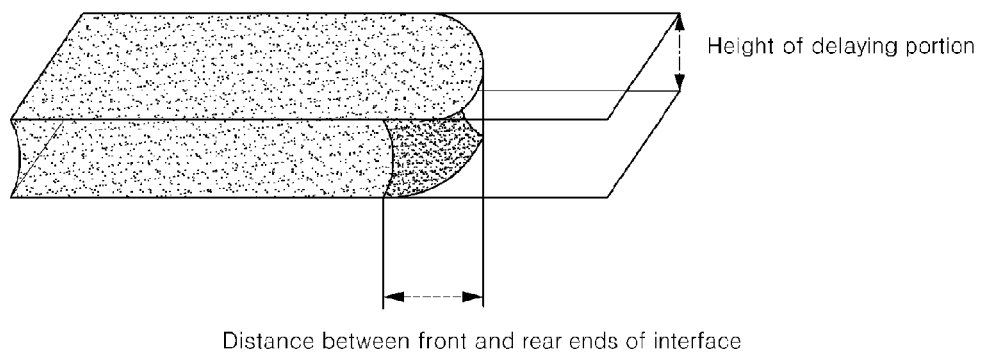
FIG. 7 is a conceptual view showing a minimal value of the slant side located at the rear of the delaying portion.
Figure 7:
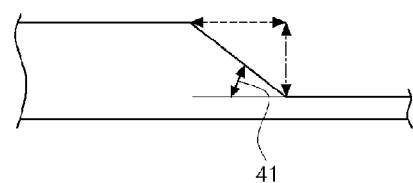

Also, the delaying portion is preferably about 3- to 20-fold taller than the microchannel. If the height of the delaying is smaller than the lower limit, only an insufficient delaying effect is obtained. On the other hand, if the height is larger than the upper limit, the fluid advances too slowly. The slant side located at the rear of the delaying portion preferably has an angle larger than an inclination angle 41 determined by the distance between the front end and the rear end of the flow interface at the narrowed part of the delaying portion and the height of the delaying portion and smaller than 90(FIG. 7). If necessary, one or more delaying portions may be provided.

Like Embodiment 1, this embodiment may have various patterns formed on the bottoms of the reservoir and the reaction portions so as to increase the surface area for the specific reaction and to improve the mixing effect.

Embodiment 3

Figure 6:
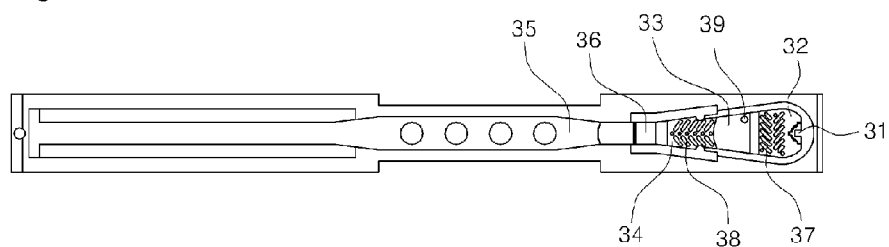
FIG. 6 is a schematic plan view showing a microfluidic chip according to a third embodiment of the present invention.

As shown in FIG. 6, a microfluidic chip for analyzing fluid samples in accordance with the present invention has a channel structure comprising a sample inlet 31 for feeding a sample therethrough, a first reservoir 32 for primarily storing the sample therein, a second reservoir 33 for secondarily storing the sample therein, a first reaction portion 34 in which a target is conjugated with a label, a second reaction portion 35 in which the labeled target undergoes a specific reaction, for example, an antigen-antibody reaction, and a delaying portion 36, located between the first and second reaction portions, for decreasing the flow rate of the sample.

This embodiment, resulting from the combination of the first and second embodiments, is adapted to prevent the sample flowing to the microchannel of the reaction portion from leaking to the extension portion thanks to the provision of the second reservoir and to delay the passage of the sample through the reaction portion thanks to the provision of the delaying portion. With such a channel structure, the microfluidic chip according to the third embodiment of the present invention can efficiently exert the wall-free function of the microchannel and afford a sufficient reaction to the sample at the reaction portion, thereby guaranteeing more accurate analysis of fluid samples. With regard to other compositions and pattern elements, reference may be made to the above embodiments.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A microfluidic chip for analyzing a fluid sample, having a channel structure comprising:
    a sample inlet that receives the fluid sample being fed into the microfluidic chip;
    a first reservoir that primarily stores the fluid sample therein;
    a second reservoir that secondarily stores the fluid sample therein when the fluid sample is received from the first reservoir;
    a first reaction portion arranged downstream of the second reservoir in which a target is conjugated with a label;
    a second reaction portion in which the labeled target undergoes an antigen-antibody reaction; and
    a delaying portion, located between the first and second reaction portions, that decreases a flow rate of the fluid sample
    wherein the first reaction portion, the second reaction portion, and the delaying portion comprise respective extension portions provided along a pair of inner sides thereof,
    wherein the delaying portion has a front portion having a slant side which becomes ascendant as it goes from the first reaction portion to the delay portion and a rear portion having a slant or vertical side connected to the second reaction portion.

2. The microfluidic chip of claim 1, wherein the microchannel ranges in height from 1 μm to 20 μm and the sample is humoral liquid including whole blood.

3. The microfluidic chip of claim 1, wherein the reservoirs have patterns formed on bottoms thereof.

4. The microfluidic chip claim 1, wherein the reaction portions have patterns formed on bottoms thereof.

5. The microfluidic chip of claim 1, wherein the height of the delaying portion is 3 to 20 times larger than that of a remainder of the channel structure.

6. The microfluidic chip according to claim 1, wherein the slant side located at the front portion of the delaying portion has an inclination of from 5 to 60 degrees.

7. The microfluidic chip according to claim 1, wherein the rear portion of the delaying portion has a slant side having an angle which is smaller than 90 degrees.

8. The microfluidic chip of claim 1, wherein the second reservoir has at least one hole formed on an upper side thereof.

* * * * *